United States Patent
Liang et al.

(10) Patent No.: US 10,993,678 B2
(45) Date of Patent: May 4, 2021

(54) SYSTEM AND METHOD FOR INTERACTIVE THREE DIMENSIONAL OPERATION GUIDANCE SYSTEM FOR SOFT ORGANS BASED ON ANATOMIC MAP AND TRACKING SURGICAL INSTRUMENT

(75) Inventors: Cheng-Chung Liang, West Windsor, NJ (US); Li Fan, Belle Mead, NJ (US); Jian-Zhong Qian, Princeton Junction, NJ (US); Xiaolan Zeng, Princeton, NJ (US); Xin Dou, Plainsboro, NJ (US); Changbo Yang, Wayne, PA (US); Guo-Qing Wei, Plainsboro, NJ (US)

(73) Assignee: EDDA TECHNOLOGY MEDICAL SOLUTIONS (SUZHOU) LTD., Suzhou (CN)

( * ) Notice: Subject to any disclaimer, the term of this patent is extended or adjusted under 35 U.S.C. 154(b) by 86 days.

(21) Appl. No.: 13/303,943

(22) Filed: Nov. 23, 2011

(65) Prior Publication Data
US 2012/0209106 A1    Aug. 16, 2012

Related U.S. Application Data
(60) Provisional application No. 61/417,001, filed on Nov. 24, 2010.

(51) Int. Cl.
*A61B 5/00*        (2006.01)
*A61B 5/06*        (2006.01)
(Continued)

(52) U.S. Cl.
CPC .......... *A61B 5/7425* (2013.01); *A61B 5/0035* (2013.01); *A61B 5/06* (2013.01);
(Continued)

(58) Field of Classification Search
USPC .................... 345/418; 600/409, 437, 544
See application file for complete search history.

(56) References Cited

U.S. PATENT DOCUMENTS

| | | | |
|---|---|---|---|
| 6,275,721 B1 * | 8/2001 | Darrow et al. | ............... 600/410 |
| 2003/0220557 A1 | 11/2003 | Cleary et al. | |

(Continued)

FOREIGN PATENT DOCUMENTS

| | | |
|---|---|---|
| CN | 1550221 A | 12/2004 |
| CN | 101001569 A | 7/2007 |

(Continued)

OTHER PUBLICATIONS

International Search Report corresponding to PCT/US11/62110 dated Mar. 9, 2012.

(Continued)

*Primary Examiner* — Serkan Akar
(74) *Attorney, Agent, or Firm* — Pillsbury Winthrop Shaw Pittman LLP

(57) ABSTRACT

A system for providing visual three dimensional assistance to a user during a medical procedure involving a soft organ. The system and method provide visual assistance to a user during a medical procedure involving a soft organ. The system and method utilize a processor for generating an image of the soft organ, a surgical instrument tracker for tracking a surgical instrument during the medical procedure, and a display in communication with the processor and the surgical instrument tracker for visually displaying in three dimensions, the image of the soft organ and the surgical instrument in relation to the soft organ.

22 Claims, 16 Drawing Sheets

(51) Int. Cl.
*A61B 34/20* (2016.01)
*A61B 8/00* (2006.01)
*A61B 8/08* (2006.01)
*A61B 5/055* (2006.01)
*A61B 6/00* (2006.01)
*A61B 6/03* (2006.01)
*A61B 90/00* (2016.01)
*A61B 34/10* (2016.01)

(52) U.S. Cl.
CPC ............. *A61B 5/062* (2013.01); *A61B 34/20* (2016.02); *A61B 5/055* (2013.01); *A61B 6/032* (2013.01); *A61B 6/466* (2013.01); *A61B 6/5247* (2013.01); *A61B 8/08* (2013.01); *A61B 8/466* (2013.01); *A61B 8/5223* (2013.01); *A61B 2034/105* (2016.02); *A61B 2090/08021* (2016.02); *A61B 2090/3908* (2016.02)

(56) References Cited

U.S. PATENT DOCUMENTS

| 2004/0034300 | A1* | 2/2004 | Verard | A61B 90/36 600/424 |
| 2005/0015005 | A1* | 1/2005 | Kockro | A61B 90/36 600/427 |
| 2005/0182319 | A1* | 8/2005 | Glossop | A61B 5/061 600/424 |
| 2006/0287595 | A1* | 12/2006 | Maschke | A61B 1/042 600/424 |
| 2007/0129631 | A1 | 6/2007 | Ma et al. | |
| 2007/0225553 | A1* | 9/2007 | Shahidi | A61B 5/064 600/103 |
| 2007/0236491 | A1 | 10/2007 | Hundley et al. | |
| 2008/0183188 | A1 | 7/2008 | Carls et al. | |
| 2008/0249395 | A1 | 10/2008 | Shachar et al. | |
| 2009/0171201 | A1* | 7/2009 | Olson | 600/438 |
| 2009/0275831 | A1 | 11/2009 | Hall et al. | |
| 2009/0281418 | A1* | 11/2009 | Ruijters | A61B 6/12 600/424 |
| 2010/0042011 | A1 | 2/2010 | Doidge et al. | |

FOREIGN PATENT DOCUMENTS

| CN | 101568294 A | 10/2009 | |
| CN | 101862205 A | 10/2010 | |
| WO | WO 2006122398 A1 * | 11/2006 | ........... A61B 5/0476 |

OTHER PUBLICATIONS

Office Action dated Dec. 31, 2014 in Chinese Application No. 2011800563701.
Extended European Search Report dated Jan. 2, 2017 in European Application No. 11842699.8.
Office Action dated Aug. 10, 2018 in EP Application 11842699.8.
Communication under Rule 71(3) EPC (Intention to Grant) dated Apr. 30, 2019 in European Application 11842699.8.

* cited by examiner

SYSTEM AND METHOD FOR INTERACTIVE THREE DIMENSIONAL OPERATION GUIDANCE SYSTEM FOR SOFT ORGANS BASED ON ANATOMIC MAP AND TRACKING SURGICAL INSTRUMENT

CROSS REFERENCE TO RELATED APPLICATIONS

This application claims priority from U.S. Provisional Application No. 61/417,001 filed Nov. 24, 2010 the disclosure of which is incorporated herein by reference in its entirety.

BACKGROUND OF THE INVENTION

Field of the Invention

This invention pertains to the interactive three-dimensional (3D) anatomic mapping in 3D space displayed on computer screens and more particularly with the aim of providing extra guidance during soft organ surgery applications.

Description of Related Art

Soft organ surgery can be difficult because there are often few external landmarks defining soft organ anatomy. Further, many soft organs contain significant vascularity. For example, a liver has few external landmarks defining hepatic anatomy and has significant vascularity. Interactive image guided surgery involves the simultaneous real-time display of intraoperative instrument location on preoperative images (computed tomography (CT) or magnetic resonance imaging (MRI)). Most of the current instrument location systems fall into the following two categories: 1) Optical tracking system, and 2) Electromagnetic tracking system. Both types of systems can provide location and orientation information and they both have some limitations: the optical tracking system needs to maintain a line of sight with the tracking sensors while the electromagnetic tracking system tends to yield to electromagnetic interference or existence of ferromagnetic materials.

There are many research projects in universities and some commercial systems that propose or provide real time image-guided surgery systems. During image-guided surgery, as the current surgical position of instruments in the operating room is registered onto medical images of the patient acquired preoperatively. These images are used as a guide by the surgeon for more accurate localization of tumors and other surrounding anatomic structures.

An image-guided surgery system typically comprises the following components: a computer system for displaying images and related information; and a physical positioning device attached to a surgical tool; the physical positioning device in communication with the computer system wherein the computer system outputs 2D images of surgical objects and the surgical tool within the images to be viewed on computer monitors.

Most of the prior systems are based on 2D imagery. Only until recently, a few systems provide 3D monitoring space. Each system may use different types of tracking devices and tools, and use different methods of registering the real environment and virtual environment. The major difference between system is the presentation of information. Many systems fail to present information in a comprehensive and efficient manner, such that their use during surgeries is under utilized. The presented information needs to be integrated and presented in such a way that users can use the information constructively and efficiently to aid in performing surgery.

SUMMARY OF THE INVENTION

In an embodiment, is disclosed, a system for providing visual assistance to a user during a medical procedure involving a soft organ. The system comprises a processor for generating an image of the soft organ, a surgical instrument tracker for tracking a surgical instrument during the medical procedure, and a display in communication with the processor and the surgical instrument tracker for visually displaying in three dimensions, the image of the soft organ and the surgical instrument in relation to the soft organ.

In another embodiment, the display further provides quantitative information during the medical procedure. In another embodiment, the quantitative information is risk analysis information or soft organ volume information. In a further embodiment, the quantitative information is at least one of the following: references information, guidance information, or alert information.

In another embodiment, the image of the soft organ includes the soft organ and other structures. In a further embodiment, the other structures include internal or external structures relative to the soft organ. In another embodiment, the image is rotatable and scalable. In a further embodiment, the display contains at least a first image and a second image.

In another embodiment, the first image is a global perspective image and the second image is a local perspective image. In another embodiment, the local perspective image is a close up view of the surgical instruments tip relative to the soft organ. In another embodiment, the first image and the second image can be synchronously manipulated.

In another embodiment, the image of the soft organ is generated based on a computed tomography (CT) image or a magnetic resonance imaging (MRI) image. In still a further embodiment, the processor overlays preoperative information on the three-dimensional image. In another embodiment, the image is combined with a second image obtained from a separate image source. In another embodiment, the second image is an ultrasound image.

In another embodiment, the processor compares the user's interactions during the medical procedure with the three dimensional image and generates a signal in response to the comparison. In another embodiment, the user's interactions include the placement of the surgical instrument in the soft organ. In another embodiment, the signal is an audio or visual alarm.

In an embodiment, a machine-readable tangible and non-transitory medium, having information for providing visual assistance to a user during a medical procedure, recorded thereon, is disclosed. Wherein when the recorded information is read, by the machine, it causes the machine to generate an image of a soft organ; track a surgical instrument during the medical procedure; and display, via a display device, in three dimensions, the image of the soft organ and the surgical instrument in relation to the soft organ.

In another embodiment, a method implemented on a machine having at least one processor, storage, and a communication platform connected to a network for providing visual assistance to a user a during a medical procedure involving a soft organ is disclosed. The method includes, generating on a display in communications with the processor, a three-dimensional image of the soft organ. Tracking, via a surgical instrument tracker, a surgical instrument during the medical procedure. Combining, via the processor, the three-dimensional image of the soft organ and the tracked surgical instrument, and displaying, in three dimensions on the display, combined image of the soft organ and the surgical instrument in relation to the soft organ.

In an embodiment, the preoperative surgical plan can be overlaid on the 3D display of the e-liver or other e-organs. For example, for liver transplantation, the system can place a pre-planned cutting surface separating the left and right liver on the e-liver displayed. During the surgery, surgeons can check how far the current cutting position has deviated from the pre-planned surface and properly make adjustments or alternations. In interventional ablation or needle biopsy, for example, a pre-planned needle entry point and the approaching route can be shown inside the e-liver. The entry point on e-liver gives doctors a quick way to determine the actual entry point in the real liver. The insertion path can be monitored, and alerts or warnings can be issued when the instrument is off route or off the target by certain predefined user preferences.

In an embodiment, the 3D environment can display the presence of the surgery instrument and its trails or paths in e-liver for surgery progress referencing and monitoring. The present system and method can provide multiple views or special views such as tool-tip view, wedge view, gun-point view, bird eye view for simultaneously viewing a target with different characteristics such as appearance, visibility of sub-structures, viewing angles, and hypothetic impact maps. The system can also overlay registered images from different modalities into one single 3D space in the 3D environment so that relative 3D spatial information is clear.

In an embodiment, the e-liver guided surgery system can be used for liver transplantation, liver resection, interventional ablation, biopsy, or embolism, or others.

DETAILED DESCRIPTION

Figure 1:
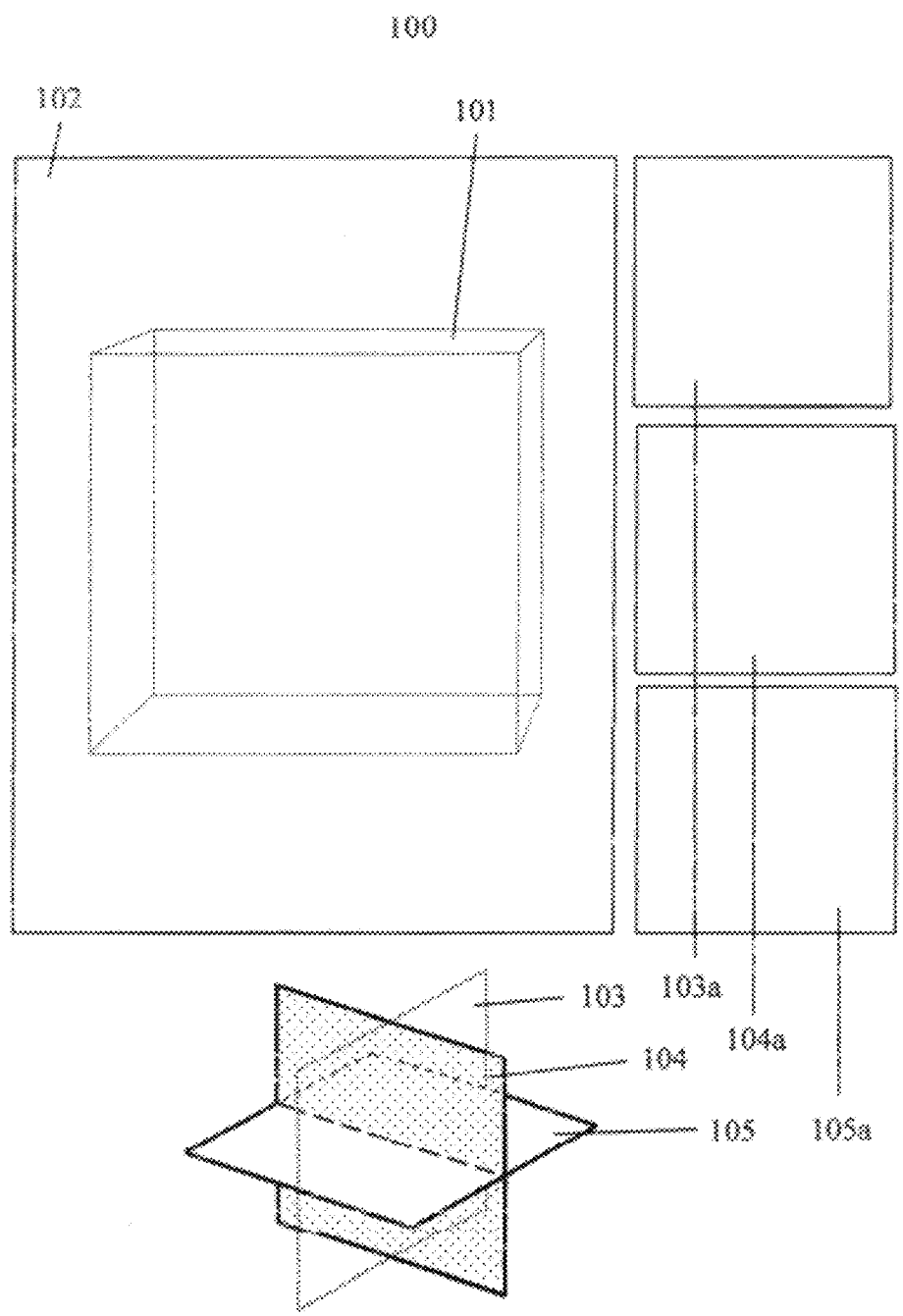
FIG. 1 depicts a graphical user-interface of the present system depicting various views and setups.

The present disclosure is directed to a quantitative interactive 3D guidance system for soft organ operations based on 3D anatomic mapping during the surgery process. Not intended as a limitation of any sort, the present disclosure references a liver as the soft organ. It is understood however, surgery and procedures on any organs such as heart, lungs, kidneys, stomach, intestines, brain, or other soft organs may utilize and benefit from the present disclosure. Accordingly, a liver is used to describe the system and method of the present disclosure.

The 3D anatomic geometric structure displays a liver, its interior and exterior vascular structures, and the surrounding objects such as vital organs or bone structures in abdominal area. For this disclosure, the 3D image of the exemplary liver will be referred to as an electronic-liver or e-liver since it is essentially a replica of the actual liver in electronic form, although any electronic organ (e-organ) could be represented. The e-liver provides a clear 3D road map for use during the process of surgery. The 3D based environment provides a unified glimpse of both global and local perspectives so that a surgeon or an interventional radiologist or interventional cardiologist knows exactly where a surgical instrument is with respect to the e-liver during an operation. During surgery, the system carefully monitors the doctor's progress as he/she works with various surgical instruments. Besides using and referencing the surgical instrument itself to determine whether enough tissue has been operated on, the e-liver with its indication of position of the surgical instrument will provide the surgeon with 3D intuitive and quantitative information and guidance on, for example, how close he/she is to a critical anatomical structure that has to be avoided during the operation or what adjustments the physicians has to make in order to follow his/her preoperative planning. Being able to see the operation instrument relative to the e-liver is important to doctors, as the actual organs are opaque and provide little spatial and quantitative information by observing the actual liver or other organ that is being operated on.

Besides monitoring the position of the surgery instrument, the system of the present disclosure also provides rich quantitative information, such as risk analysis and quantitative measurements/volumetry, for references, guidance, or alerts during the operation. The e-liver can provide virtual infra-structures such as liver lobes or anatomic/fudicial marks for referencing during the surgery. It can provide impact awareness at critical junctures. Further, because all the geometric objects inside the e-liver are well-defined, their associated numerical volume measurements are readily available. Further, during any well-defined alternations or operations such as cutting an organ into separated pieces, the numerical volume value of each individual piece is also available right away. Distance measurements between two different points in e-liver or other e-organ can also be calculated. Based on quantitative analysis, the present method and system can provide just-in-time functional impact of liver regions. For example, when a user "pinches" a vascular branch in the e-liver, the system can calculate the affected down flow region in an interactive and real-time fashion, and may display to the user geometric regions and associated quantitative volumetry, and the associated risk. That way, the user may decide whether there is any risk if operation plan is changed during the procedure.

3D Environment for E-Organs

Figure 2:
FIG. 2 depicts an E-liver displaying a segmented liver and internal vascular systems in accordance with the present disclosure.

As depicted in FIG. 1 E-liver resides in a 3D environment within computer screen 100. It is a 3D scene 101 perceptively even though it is displayed on a 2D screen. Within this 3D scene, the segmented objects of the e-liver, as depicted in FIG. 2, can be seen on screen 100. The liver surface 200, the vascular systems 201, and the many branches 202 and other masses or objects 204 are displayed in 3D. Individual 3D planar views 103-105 of the respective components making up the e-liver may be displayed individually in 3D on screens or windows 103a-105a. The whole e-liver scene (depicted by object 101) can be rotated and zoomed by computer mouse control or other means of zooming and rotating an image on a computer screen such as trackball, touch screen, or joystick. When the scene in window 102 is rotated and zoomed, the respective 3D objects 103a-105a within the scene are rotated and zoomed accordingly.

Figure 3:
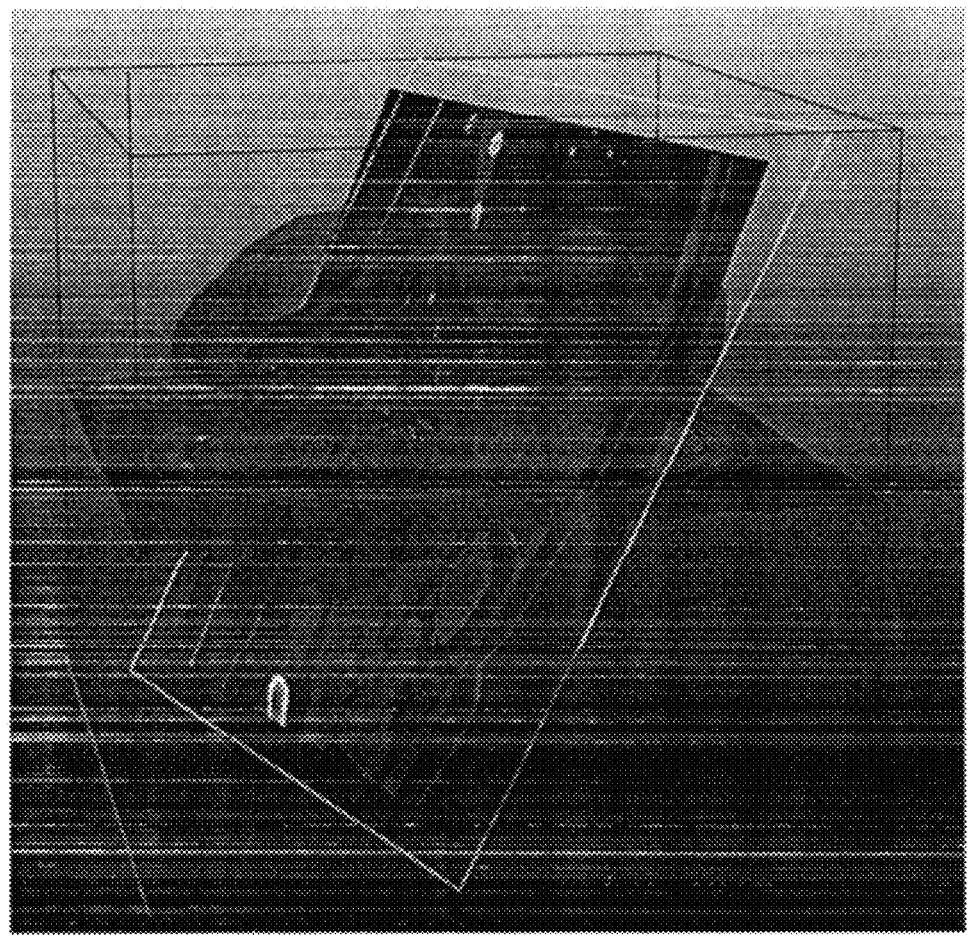
FIG. 3 depicts an image and MPR residing in a 3D environment in accordance with the present disclosure.
Figure 4:
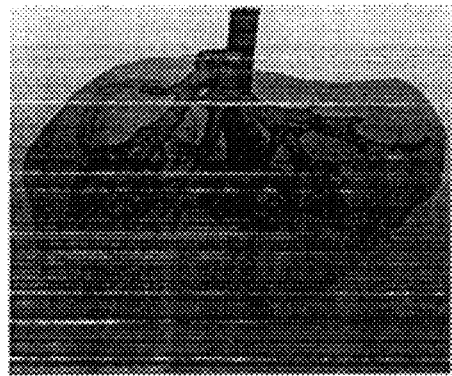
FIG. 4 depicts multiple objects and views of an E-liver in accordance with the present disclosure.
Figure 4:
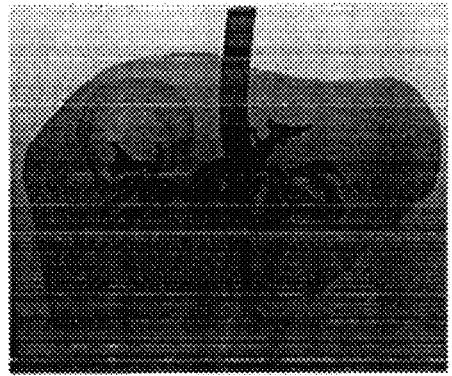
Figure 4:
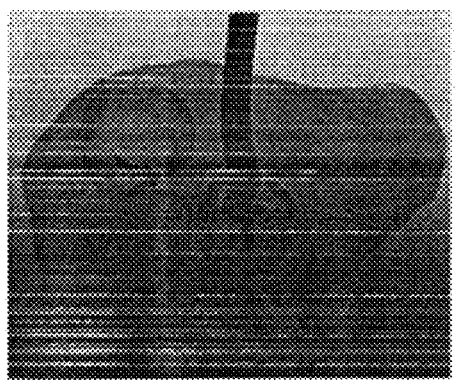
Figure 4:
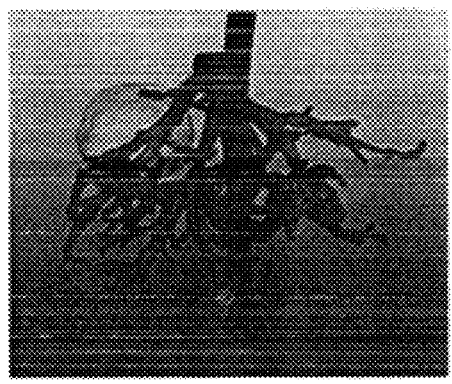

In the 3D scene, the 2D images either from the original scanned images or composed multiple-planar re-projection (MPR) images can be overlaid within the scene and among the segmented objects as seen in FIG. 3. The integration of 2D images and 3D objects can provide users intuitive 3D spatial senses among segmented objects and data volume. The images within the scene can be interactively moved to different location to reveal spatial relationship in a particular area.

The visibilities of 2D images and individual segmented objects can also be-interactively modified to reveal some focus objects or areas and hide other less relevant objects. Each segmented object can be interactively changed to display as opaque (as in 4a), transparent, or invisible (as in 4c-d).

Figure 5:
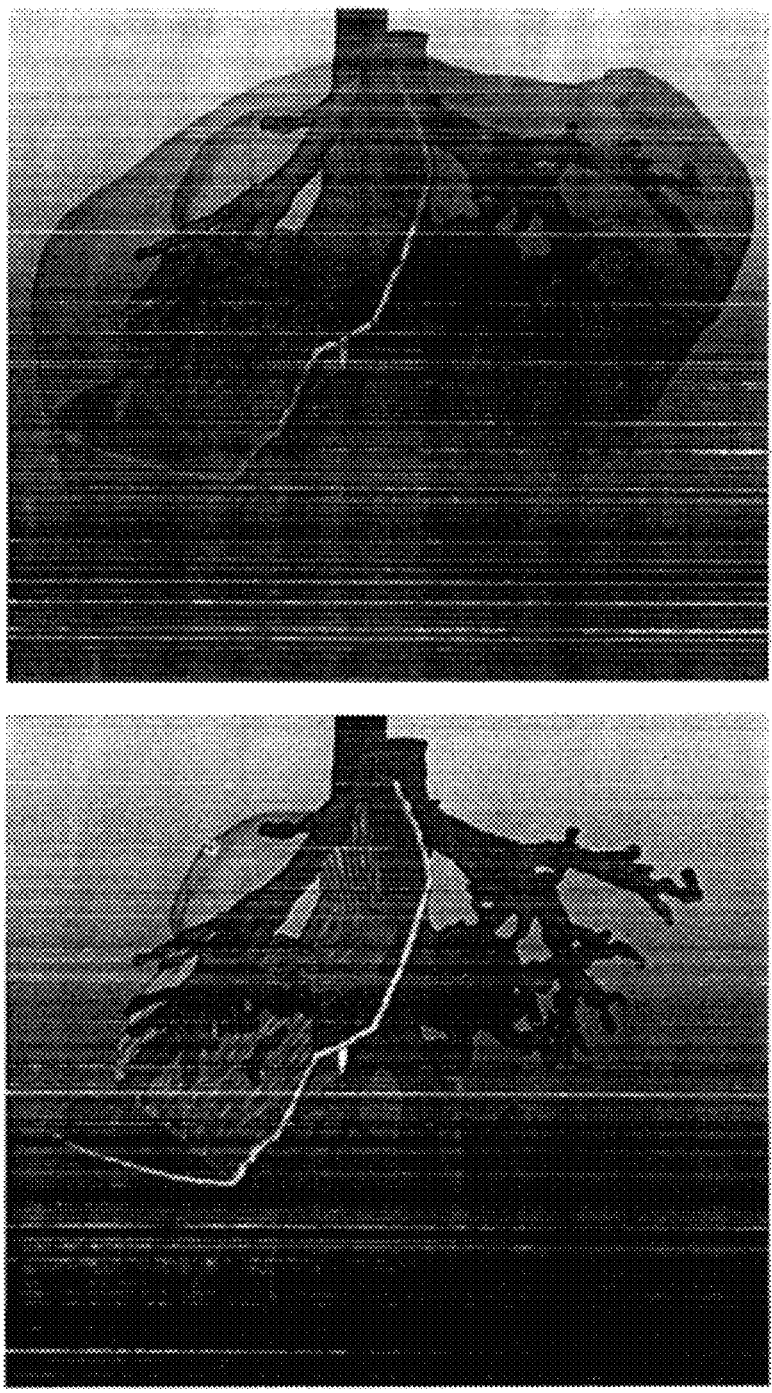
FIG. 5 depicts an E-liver with various preoperative surgical resections surfaces and surgical instruments in accordance with the present disclosure.
Figure 6:
FIG. 6 depicts a preoperative entry point on an E-liver, the insertion route, and the target for interventional liver treatment in accordance with the present disclosure.

Aside from segmented objects used to form data volume, other supporting objects or artificial objects can be placed inside the 3D scene. For example, artificial fudicial marks can be interactively placed inside the 3D scene relative to the e-liver Such as to place marks at branch points of vascular structures within e-liver; or using a tracking device to mark points on the real liver surface and the corresponding points can be displayed on the e-liver surface. FIG. 5a-b depicts preoperative surgical plans such as resection surface for liver resection or liver transplantation, or entry point, insertion route. Surgical plans can either be imported from another surgical planning platform or done in a planning module attached. Interactive tools are provided in the planning module to allow user to enter a plan and receive real-time analysis of the plan so the user can modify it accordingly. FIG. 6 depicts an e-liver and a target point 601 for interventional treatment like ablation or needle biopsy can be displayed within the 3D scene together with the segmented objects.

Figure 8:
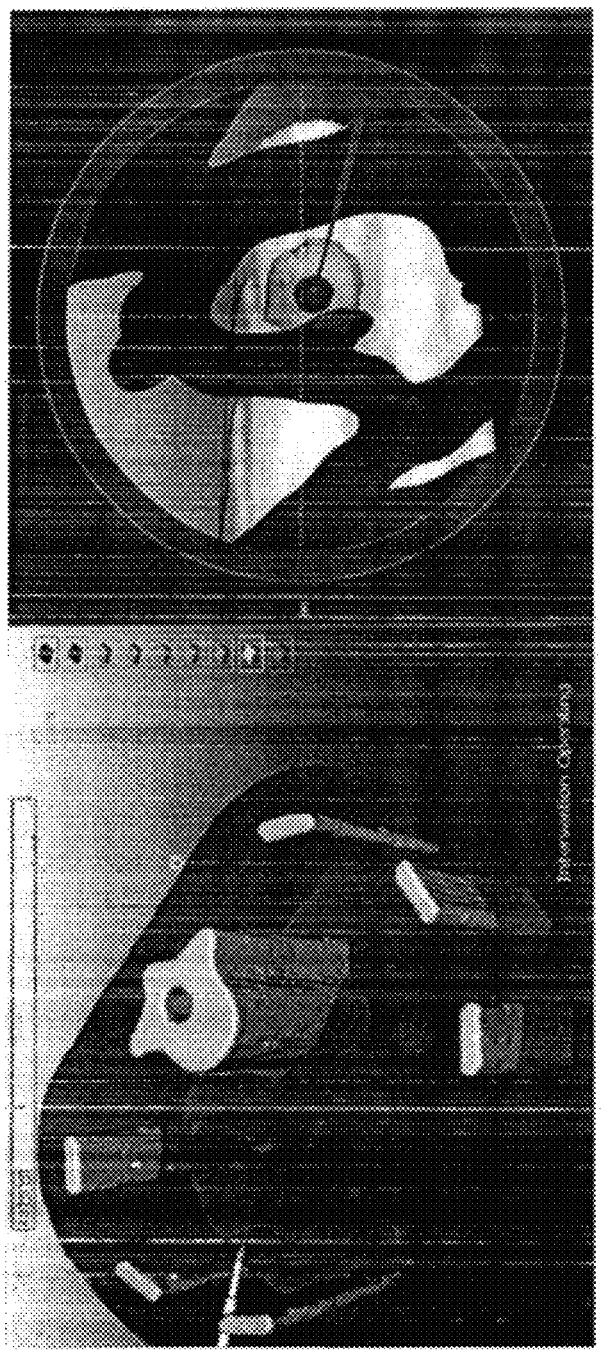
FIG. 8 depicts a global view of an E-liver with a tool-tip in local view in accordance with the present disclosure.

During an operation, the virtual surgical instruments, including their positions/locations and orientations, can be shown within the 3D scenes (see FIG. 8 a) to reveal the relative spatial relationship of the actual instruments with respect to the operated objects and other reference objects. For electromagnetic tracking, non-ferromagnetic instrument without electromagnetic interference emission can be tracked by either attaching a sensor to any part of the instrument if the instrument is rigid or to the tip if the instrument is rigid. It should be noted that in existing optical tracking systems only rigid instrument can be tracked. When the tracking sensor is attached to part other than the instrument tip, an additional calibration procedure needs to be carried out to determine the relative position between the sensor and the instrument tip. Examples of instruments that can be tracked include biopsy needle, ablation applicator, catheter, scalpel, CUSA (Cavitron Ultrasonic Surgical Aspirator), and ultrasound transducer. The moving trail of the instrument can be recorded and displayed inside the 3D environment to show the progress of surgery and relative positions with respect to the preoperative plan, and the discrepancies between the actual cutting surface and the pre-planned surface.

Figure 7:
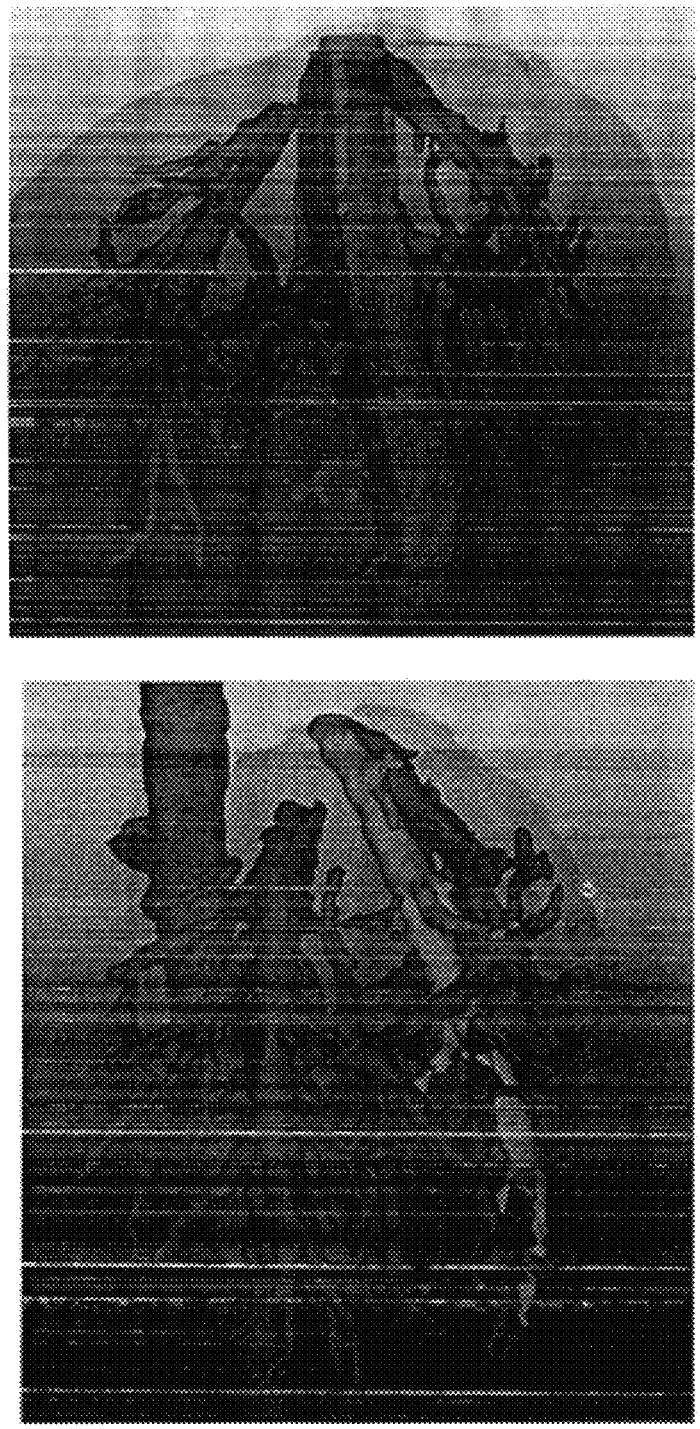
FIG. 7 depicts an exemplary work zone region on an E-liver in accordance with the present disclosure.

For liver resection and transplantation, a work zone 701 as seen in FIG. 7a is defined within a margin of the preoperative resection surface. This work zone indicates a critical area for the surgery. It is the area that a doctor will operate most of the time. All the cuts of critical vessel branches should happen in this zone. A margin can be preset by the user or can be automatically calculated from the pre-operative plan. As seen in FIG. 7b, the critical vessel branches 702 within the work zone 701 are highlighted with different appearance from the rest of branches outside of the work zone.

3D Environment Enhancement with Other Focused 3D Views

FIG. 8a depicts a global view of the 3D environment and tool. Other more focused perspectives can be used to enhance understanding spatial relationship of a particular area.

FIG. 8b depicts a tool-tip view of the present disclosure. This view afford the user a view from the tip of the surgical instrument and looks forward directly. It provides a perspective so that users can see the structures surrounding the instrument tip. Users can use it as reference to avoid important anatomic structures or have clearer understanding of the spatial and geometric relationship to proceed. The circular shape 800 of the view gives user a sense of magnified glass feeling. The cross-hair 801 gives the aim center of direct forward movement. The border of the circular view 802 provides spaces for in-scene controls and the color is used as alert notification. In an embodiment, when the moving is on target, the color is green. When the moving is off target, the color is changing from green to orange to red according to how far off the target.

Figure 9:
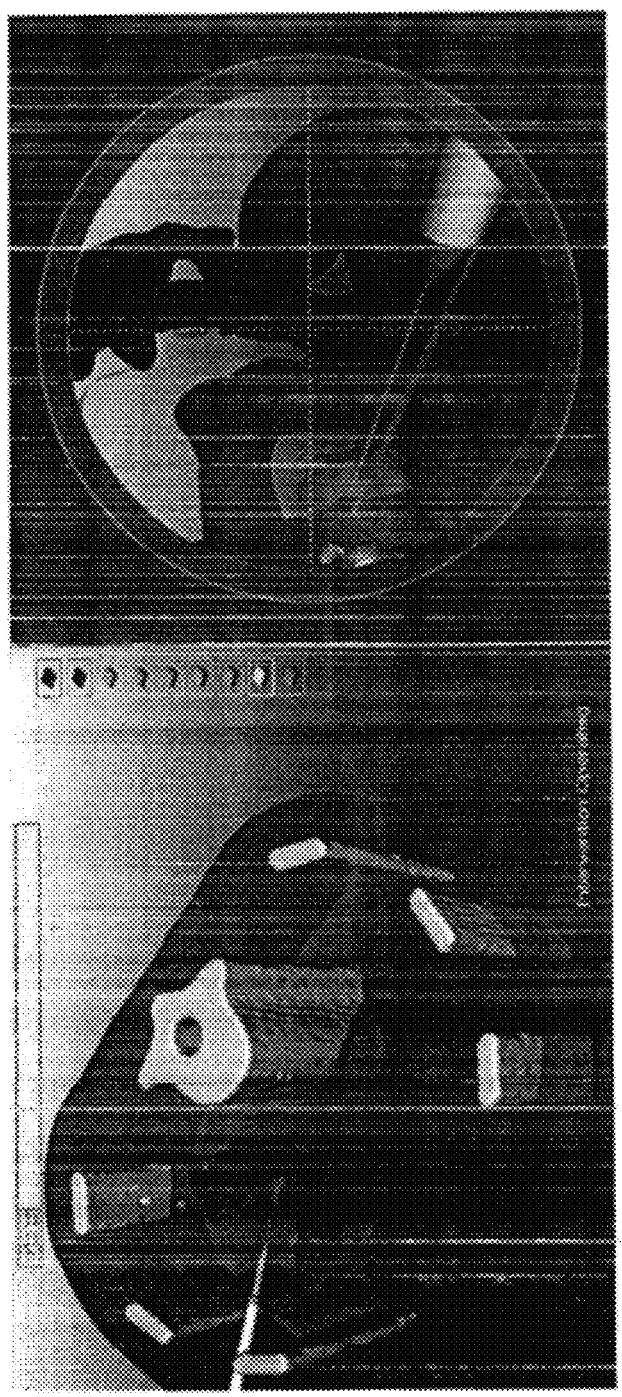
FIG. 9 depicts a global view of an E-liver with an oblique tool-tip local view in accordance with the present disclosure.

FIG. 9 depicts another embodiment with a near tool-tip view. In the view depicted in FIG. 9 the user is presented with a view from a small distance back from tool-tip and with a little skew angle from the straight of the tool. In an embodiment, the distance back from the tool-tip can further be associated with the model of operation instrument. For example, during a radio frequency ablation (RF ablation) operation, the center of the ablation treatment region is often certain distance back from the tool tip. Therefore, the system may request that a user input the model of the ablation tool to be used and automatically set the distance based on the manufacture's instructions or specification. In another embodiment, the system may request the user to set a distance manually. This view let user see a portion of tool front to the center of the view. It gives users more sense of the tool with respect to its surrounding structures.

In another embodiment, the view is a view that has a pre-set view angle perpendicular to the tool-tip view or near tool-tip view and has the entire tool in plane. It provides an overview of the location and orientation of the instrument and gives user intuitive information on whether the instrument will hit the target or other anatomic structures, and the distance to hit the target/an anatomic structure.

Figure 10:
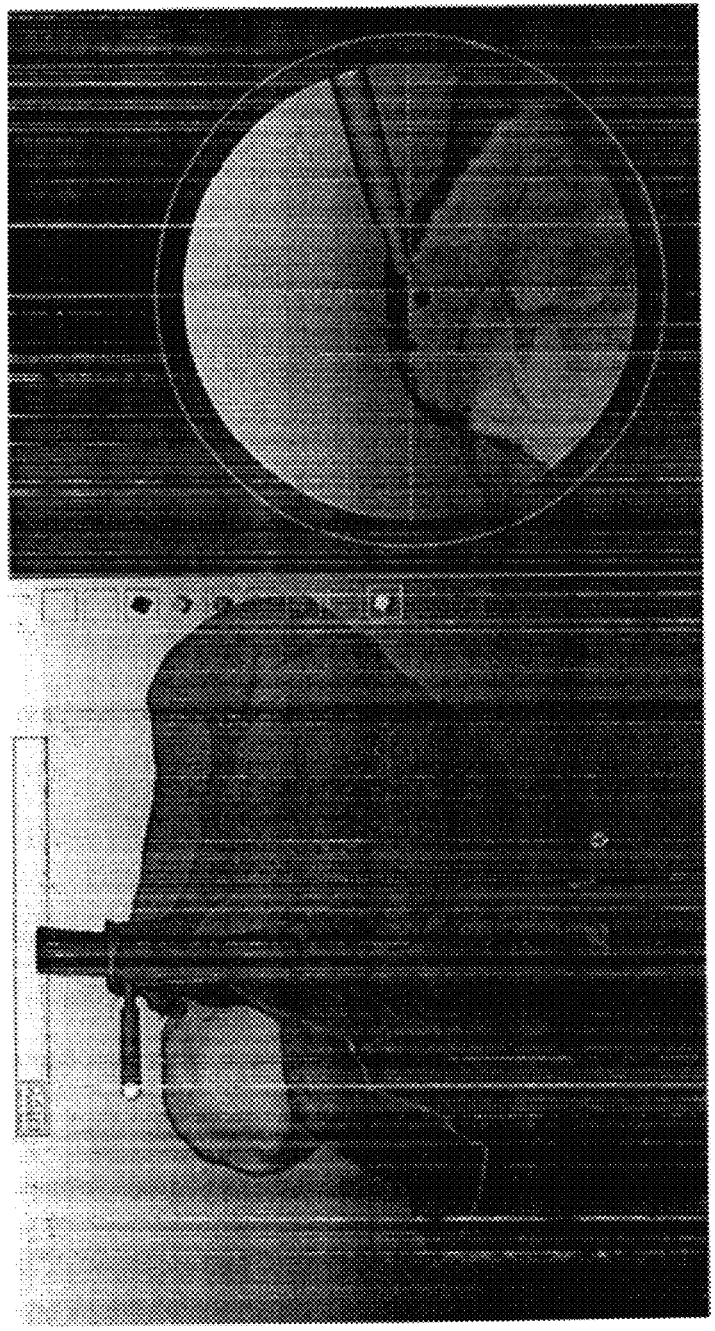
FIG. 10 depicts a global view of an E-liver with a zoom-in local view in accordance with the present disclosure.

In another embodiment, depicted in FIG. 10, another focused view is a view that zooms to near the tool tip but with a viewing angle more aligned with the global view. This view lets users see more closely into the surroundings near the surgical instrument. The local view can be rotated independently but it can also be synchronized with the global view so that when rotating, both views have the same viewing angle.

In another embodiment, the focused or local view is a view which shows only the anatomies with a wedge shaped view at the tool tip. In this embodiment, the system may determine the orientation of the wedge based on the position and orientation of the tool, information of the already operated regions, as well as the pre-operative plan. For example, in a tumor resection or transplantation case, the system records all the trail of the tool tip positions. The order of positions in the trail indicates how a user cuts along a cutting surface, for example, cutting towards a specific direction. In an embodiment, the system can, "on-the-fly" estimate the current user cutting direction from the tool tip positions recorded within a certain time period. By combining the cutting direction estimation information with the current tool tip position, the system can determine the location and orientation of the wedge, and further display the anatomic structures therein. The wedge view can also be extended to along the entire cutting surface, instead of a local view.

In an embodiment, by clicking on a button, the view angles between a global view and a local view, or among all the view modes can be synchronized, i.e., no matter how the user rotates in one 3D display, the other views rotate accordingly. Alternatively, the user can un-synchronize the views, make adjustments on each individual display window, and re-synchronize them. Such synchronized or unsynchronized adjustments can be done to other display parameters, such as zoom-in factor.

In an embodiment, the orientation of, and other anatomic structures displayed in the local view may be automatically aligned with the real patient position. This can be done by attaching a position sensor to the patient so the patient position can be computed by fixing the electromagnetic field generator or optical tracking cameras to a known orientation. For example, in an embodiment, if a patient is in a supine position, then the local view shall be so planned so that the up direction corresponds to the front of the patient. Head, feet, left, right, anterior, and posterior directions can also been indicated in the local view as applicable. In an embodiment, the orientation can be adjusted by users to fit their particular vantage point. For example, when a patient is in a supine position and the doctor is standing on the right side of the patient, the patient head direction is roughly on the left of the local view. But if the doctor is standing on the left side of the patient, the patient head direction is on the right of the local view. By doing so, a user can intuitively determine towards which direction should he/she adjust the tool position or orientation so that he/she can hit the target or better follow the plan previously determined.

3D Integration with Other Image Modality

Figure 11:
FIGS. 11 a-b depict an ultrasound image overlay in a 3D scene in accordance with the present disclosure.

FIG. 11a depicts an embodiment where the use of other modality images such as ultrasound images (FIG. 11b) are used and rendered inside the 3D environment together with original volume and segmented objects. Live ultrasound images may be streamed from an ultrasound imaging source to the present system. After a registration process is completed, the subsequent ultrasound images can be overlaid inside the 3D environment with proper orientation and location so the images seem to fan out the ultrasound transducer, which is also shown as a 3D model in the 3D environment. Another option is to show the ultrasound images with their registered MPR CT images, either in a side by side view mode or in an overlaid mode so the user can have a better comparison between the two modalities. The spatial relationship of the images and segmented objects can be perceived in 3D. It is more intuitive than most of the 2D image based systems which needs to project segmented objects or surgical instrument on the plane of the image and lost the direct visual sense of 3D geometric and spatial relationship. Besides ultrasound images, functional images such as PET and SPECT images can also be combined to achieve better guidance.

Real-Time Quantitative Guidance

Figure 12:
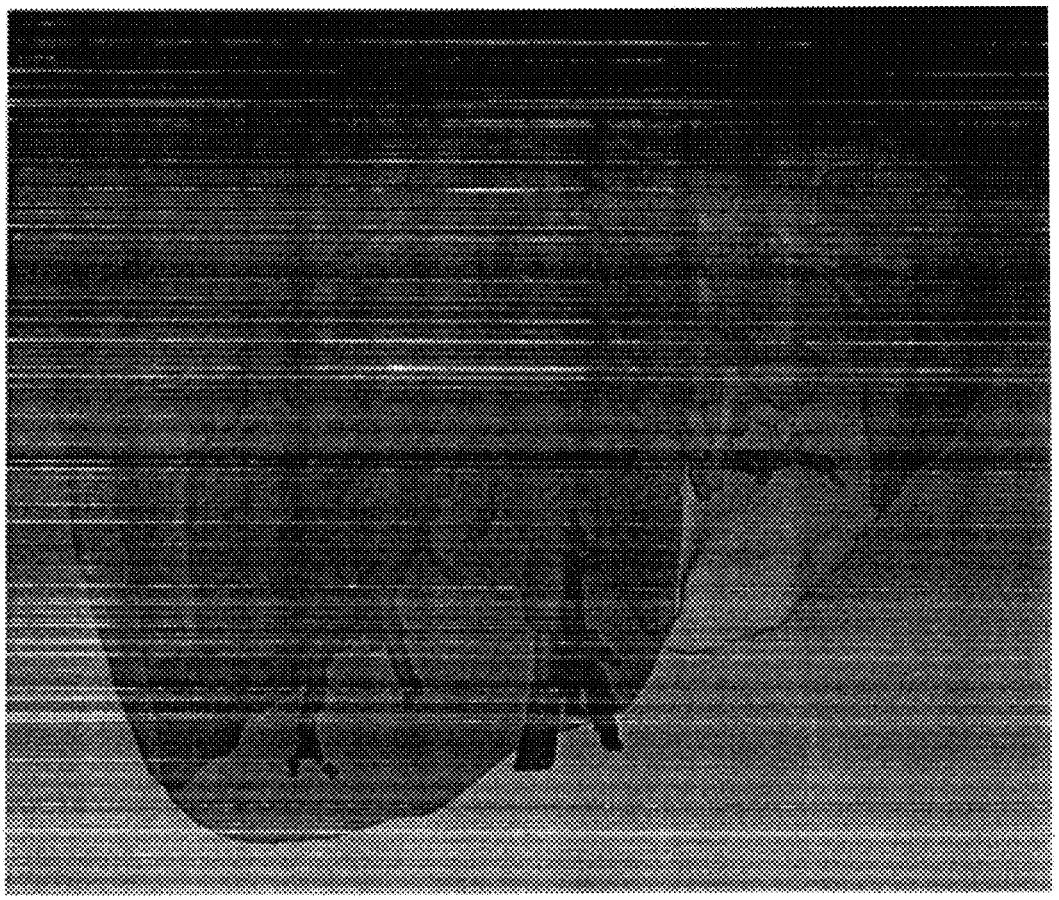
FIG. 12 depicts an E-liver with various liver lobes in accordance with the present disclosure.

FIG. 12 depicts an embodiment where virtual infrastructure such as liver lobes can be overlaid with e-liver as references for surgery. Liver lobes can be created and segmented during pre-operative surgical planning. The liver lobes can either be segmented with user's experience using planes or curved surfaces or from vessel territory analysis.

E-liver provides just-in-time functional impact region information. Point-of-interest (POI) can be critical anatomic structures that a user wants to avoid or to go through during the operation, or structures that may cause clinical significance if affected. In the liver operations for example, POIs can be critical vessel branches (including hepatic vein, portal vein, hepatic artery, bile duct) or other organs or anatomic structures. In one embodiment, during the pre-operative review or during the operation, the user can define various POIs, by clicking on the corresponding locations on the 3D e-liver or 2D original images. In another embodiment, a POI can also be automatically defined by the system. For example, in an ablation case, if a treatment region affects a nearby vessel branch, the vessel branches can be automatically added into the POI list.

When the user navigates close to a pre-defined POI, the system will automatically calculate the territory, including its shape and volume of the vessels starting from this POI down to all connected sub-branches. The territory is the liver region drained or supplied by that vessel and its sub-branches. To calculate the territory based on a POI which is a point on the surface of the vascular structure, the system may calculate its diameter from the start point to the other side within this vascular structure. Since there are variations across the vessel, the system may take a median length among a small neighborhood of the POI as the diameter. Once the diameter is determined, the system will search several cross-sectional planes that enclose the diameter line and calculate the cross-sectional region of the plane with the vascular structure. The area with the most circular region is chosen as the best cross-sectional plane. This cross sectional plane then cuts the vascular structure into two separated sections.

Figure 13:
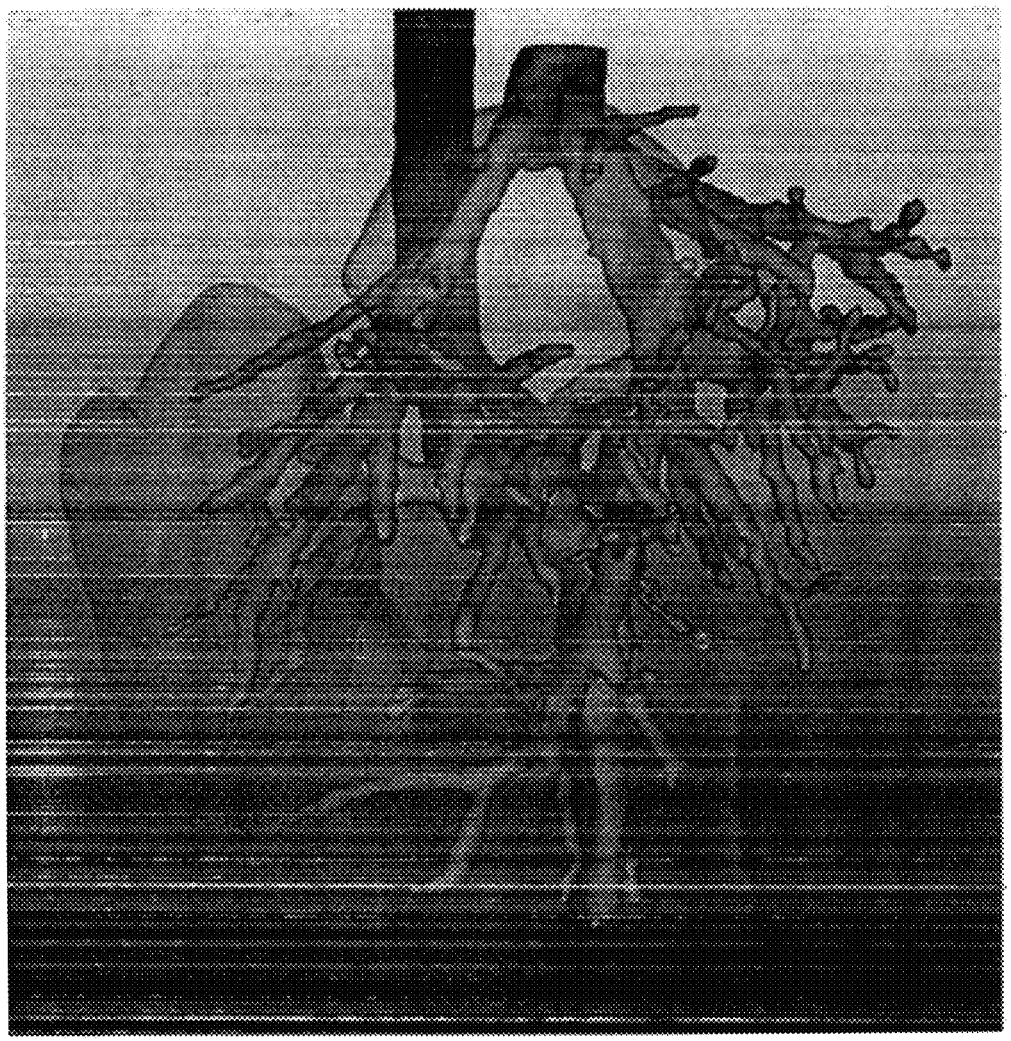
FIG. 13 depicts a just-in-time functional impact region in accordance with the present disclosure.

The section that does not contain the root of the vascular structure is used to calculate the down flow region. As seen in FIG. 13, the down flow region is calculated based on minimum distance principle. For each voxel inside the liver, the minimum distances to the part of down flow vascular structure and the other parts are calculated. The voxel is said to belong to the part where the distance is smaller. In this way, a down flow region can be defined from all the voxels that are closer to the down flow parts of the vascular structure.

In an embodiment, animation of flow out from POI to the border of impact region is generated to provide a visual just-in-time impression. The animation is created by a sequence of morphological dilation and Boolean- and operations. The system uses a 3D binary mask (V) of vascular tree from POI cutting point, a calculated down-flow region mask (T) and the cutting point (P). The animation sequence is generated as follows:

Let $A0=P$.
While (volume($A_{i+1}$)<volume(V))
Do $A_{i+1}$=Dilate($A_i$) & V; record $A_{i+1}$.
$B0=A_{i+1}$
While (volume($B_i$)<volume(T))
Do $B_{i+1}$=Dilate($B_i$) & T; record $B_{i+1}$.

The final animation sequence is A0, A1, . . . , B0, B1, . . . , T.

The interval or frames of animation can be controlled by the size of dilation kernel. A smaller kernel produces a smoother but lengthier sequence while a larger kernel produces a sparse but shorter sequence.

In another embodiment, after the system records all the trails of the tool tip positions, the locations in the trails are mapped onto e-liver. They can also be shown in the 3D e-liver display to indicate to the user the path already operated. In tumor resection or liver transplantation case, the trails represent the actual cutting surface from the operation. The system can also establish an interim cutting surface by combining the actual cutting surface in the already operated region with the portion of the pre-planned surface in the region to be operated. The volumes of the remnant and resection liver or the left and right liver can be calculated as the liver portion to one side of the interim cutting surface.

In one embodiment, the system perform quantitative risk analysis in real-time during operation. The analysis is based on the record of the region already cut through and the instrument's current position relative to critical structures (e.g. large vessels, lesion safety margin, etc.). Based on these information, together with the ability of territory analysis and liver functional analysis, the system can provide warnings ranging from simple close-to-vessel or out-of-safety-margin warnings to complicate remaining functional liver volume information. In another embodiment, the system highlights the critical anatomic structures for user to pay special attention too. For example, when user navigates close to a pre-defined POI, the POI is highlighted on the 3D e-liver display by either changing its color to a more visible one, or enlarging its size. In another embodiment, while the user is operating on the real patient, the system automatically highlights all the anatomic structures within certain distance from the tool tip on the 3D e-liver display and/or on 2D original image display. The highlighting can be done by changing the 3D rendering colors of the anatomic structures to alert the user. In an ablation case, a sphere of the size of the ablation treatment effective region can be rendered to highlight the anatomic structures. The same techniques can be applied to the highlighting on the 2D display.

In one exemplary embodiment, the system forecasts if the user may miss or hit the target under the current operation and give warnings or confirmations. For example, in an ablation case, when user starts the needle position, the system can calculate if the current needle position is close enough to the pre-defined entry point. If not, the system can give audio or visual warning, signals/signs. In an embodiment, based on the tip position and the orientation of the needle, the system can forecast the needle path by extending the needle forward along its current orientation. The system can then estimate if the forecasted needle path will hit or miss the preset target and give warning signs/signals in case of a miss or anticipated. As the needles penetrates the organ, if the forecast needle path indicates the user may hit a critical anatomy, the system can also highlight the said anatomy and give audio or visual warning. If the needle tip hits the pre-defined target, the system may give confirmation. However if after the hit the needle passes the target the system can give warning again.

In a case of a tumor resection or liver transplantation, the system, in real-time may determine if the tool tip is within the work zone. The work zone is defined to be the safe operation region with confined offset from the pre-planned cutting surface. The system may give warning when the tool tip is out of the work zone. In another embodiment, whenever the system determines that a vessel is-affected-differently than pre-planned, it can automatically perform the territory analysis, calculate associated volumes, and update the volumes of each portion of the liver. If one portion of the liver has a volume smaller than a safe level, the system can give warning.

Volume Measurement and Distance Measurement

Figure 14:
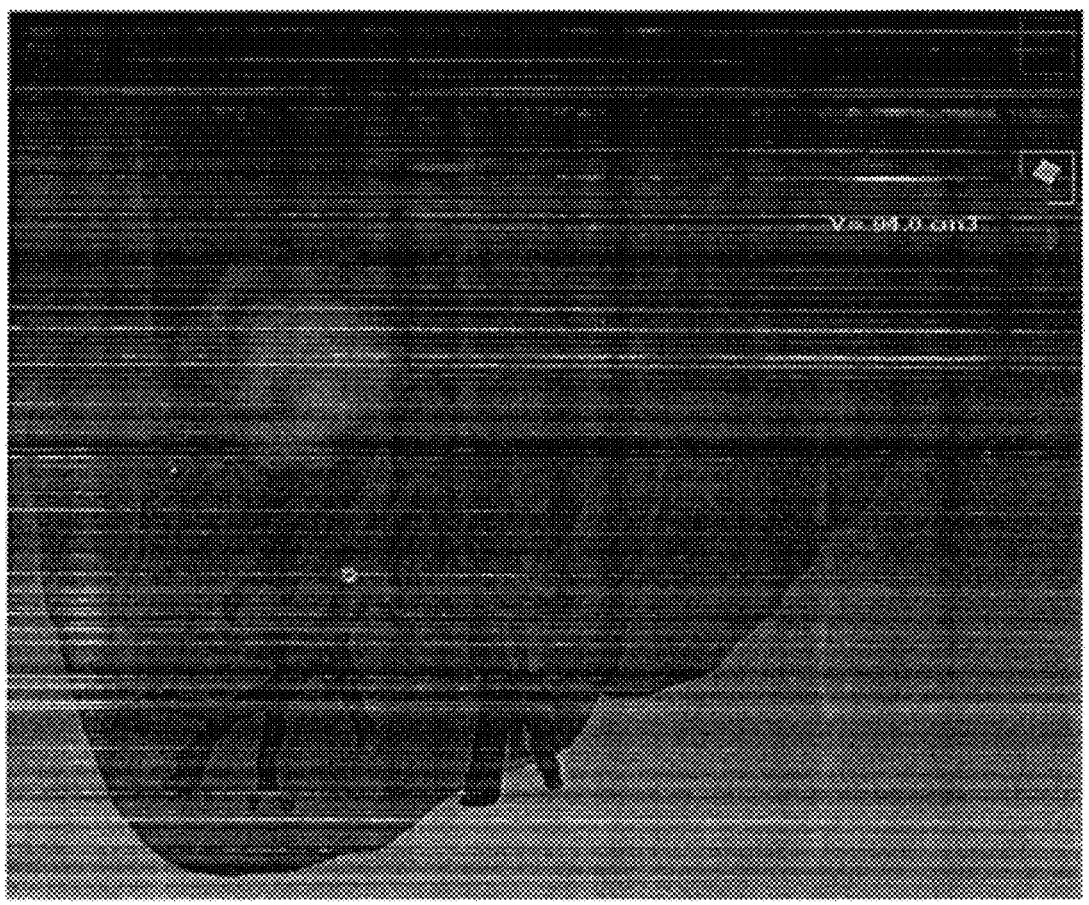
FIG. 14 depicts an E-liver display with a volume measurement in accordance with the present disclosure.

Each piece of a segmented object is composed of voxels that are labeled as a particular kind of object. The numerical value of the volume of each segmented object is the sum of the labeled voxels multiplied by the physical size of a voxel. In an embodiment, the physical size of a voxel can be obtained or calculated from the information coming along with the scanned images. The volume information may be stored with each segmented object in an electronic data structure in e-liver. As seen in FIG. 14, whenever a user needs to see the numerical volume value of an object, the user can select the object or the associated object controller and the system will display the volume value in a visual display, such as a popup message, sub window, table, or message, somewhere in the system display.

Figure 15:
FIG. 15 depicts an E-liver display with a distance measurement between points in the E-liver, in accordance with the present disclosure.

Similarly, in an embodiment depicted in FIG. 15, the distance between any two points in the 3D scene is available to the user, since each point represents a voxel and its coordinate in 3D space is defined. Two points may be selected by the user and the distance between two points is then calculated based on 3D geometric formula of two coordinates and is displayed to the user.

Figure 16:
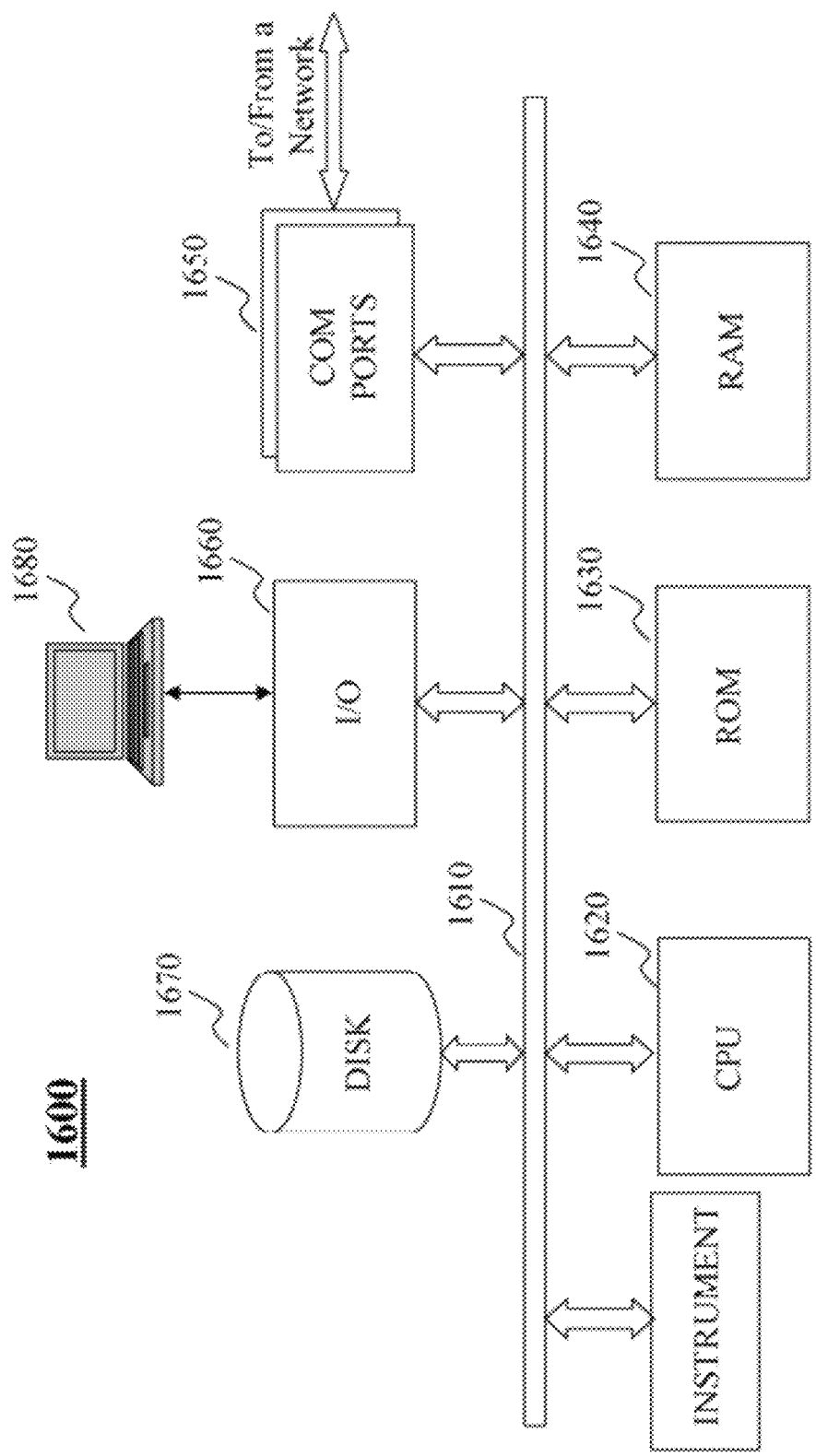
FIG. 16 depicts a computer system for carrying out the system and method of the present disclosure in accordance with the present disclosure.

FIG. 16 depicts a general computer architecture on which the present teaching can be implemented and has a functional block diagram illustration of a computer hardware platform which includes user interface elements. The computer may be a general purpose computer or a special purpose computer. This computer 1600 can be used to implement any components of the interactive three-dimensional anatomic mapping in 3D space and surgery assistance as described herein. For example, the three dimensional mapping, image display, image storing, instrument tracking, volume and distance computations, can all be implemented on a computer such as computer 1600, via its hardware, software program, firmware, or a combination thereof. Although only one such computer is shown, for convenience, the computer functions relating to the disclosure described herein may be implemented in a distributed fashion on a number of similar platforms, to distribute the processing load.

The computer 1600, for example, includes COM ports 1650 connected to and from a network connected thereto to facilitate data communications. The computer 1600 also includes a central processing unit (CPU) 1620, in the form of one or more processors, for executing program instructions. The exemplary computer platform includes an internal communication bus 1610, program storage and data storage of different forms, e.g., disk 1670, read only memory (ROM) 1630, or random access memory (RAM) 1640, for various data files to be processed and/or communicated by the computer, as well as possibly program instructions to be executed by the CPU. The computer 1600 also includes an I/O component 1660, supporting input/output flows between the computer and other components therein such as user interface elements 1680. The computer 1600 may also receive programming and data via network communications.

Hence, aspects of display and assistance during soft organ surgery, transplant and procedures as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution. In addition, the 3D software and analysis and tracking components as disclosed herein can be implemented as a firmware, firmware/software combination, firmware/hardware combination, or a hardware/firmware/software combination.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A system having at least one processor, storage, and a communication platform connected to a network for providing visual assistance to a user during a medical procedure involving a soft organ, the system comprising:
    a processor, configured to segment the soft organ and surrounding anatomical structures of the soft organ from image data obtained from a patient, and generate a three dimensional image of the soft organ and the surrounding anatomical structures based on the segmentation;
    a surgical instrument configured to move inside the patient's body during the medical procedure;
    a sensor configured to
        track location and orientation of the surgical instrument when the surgical instrument moves inside the patient's body during the medical procedure,
        place a corresponding virtual surgical instrument, based on the tracked location and orientation of the surgical instrument, in a 3D scene to reveal a relative spatial relationship of the surgical instrument with respect to the soft organ, and
        generate one or more images based on location and orientation of the corresponding virtual surgical instrument in the 3D scene, wherein the one or more images represent close-up views acquired from certain distance back from the tip of the virtual surgical instrument, and the distance is set based on an input from the user;
    wherein at least one in-scene control is embedded in a border of at least one of the one or more images; and
    a display, implemented on the at least one processor, in communication with the processor and the sensor and configured to provide visual assistance during the medical procedure by simultaneously displaying the three dimensional image with the surgical instrument visualized therein in relation to the soft organ and the surrounding anatomical structures and the one or more images.

2. The system of claim 1, wherein the display further provides quantitative information during the medical procedure.

3. The system of claim 2, wherein the quantitative information is risk analysis information.

4. The system of claim 2, wherein the quantitative information is soft organ volume information.

5. The system of claim 2, wherein the quantitative information is at least one of the following:
references information,
guidance information, or
alert information.

6. The system of claim 1, wherein the surrounding anatomical structures include internal or external structures relative to the soft organ.

7. The system of claim 1, where the three dimensional image is rotatable and scalable.

8. The system of claim 1, wherein the simultaneously displayed three dimensional image and one or more images are synchronously manipulated.

9. The system of claim 1, wherein the three dimensional image of the soft organ is generated based on a computed tomography (CT) image or a magnetic resonance imaging (MRI) image.

10. The system of claim 1 wherein the at least one processor overlays preoperative information on the three dimensional image.

11. The system of claim 1 wherein the three dimensional image of the soft organ is combined with another image obtained from a separate image source.

12. The system of claim 11, wherein the other image is an ultrasound image.

13. The system of claim 1, wherein the at least one processor further compares the user's interactions during the medical procedure with the three dimensional image and generates a signal in response to the comparison.

14. The system of claim 13, wherein the user's interactions include placement of the surgical instrument in relation to the soft organ and the surrounding anatomical structures.

15. The system of claim 13 wherein the signal is an audio or visual alarm.

16. The system of claim 1, wherein the surrounding anatomical structures of the soft organ are selected by the user before or during the medical procedure.

17. The system of claim 1, wherein the surrounding anatomical structures of the soft organ are highlighted on the three dimensional image.

18. The system of claim 1, wherein a viewing angle of the one or more images is aligned with a position of the patient during the medical procedure.

19. The system of claim 1, wherein a viewing angle of the one or more images is aligned with a viewing angle of the three dimensional image.

20. The system of claim 1, wherein the tip of the surgical instrument is not visible in the one or more images.

21. A non-transitory machine-readable medium, having information for providing visual assistance to a user during a medical procedure, recorded thereon, wherein the information, when read by the machine, causes the machine to perform the following:
segmenting a soft organ and surrounding anatomical structures of the soft organ from image data obtained from a patient;
generating a three dimensional image of the soft organ and the surrounding anatomical structures of the soft organ based on the segmentation;
tracking location and orientation of a surgical instrument when the surgical instrument moves inside the patient's body during the medical procedure;
placing a corresponding virtual surgical instrument, based on the tracked location and orientation of the surgical instrument, in a 3D scene to reveal a relative spatial relationship of the surgical instrument with respect to the soft organ;
generating one or more images based on location and orientation of the corresponding virtual surgical instrument in the 3D scene, wherein the one or more images represent close-up views acquired from certain distance back from the tip of the virtual surgical instrument, and the distance is set based on an input from the user;
wherein at least one in-scene control is embedded in a border of at least one of the one or more images; and
simultaneously displaying the three dimensional image with the surgical instrument visualized therein in relation to the soft organ and the surrounding anatomical structures and the one or more images.

22. A method implemented on a machine having at least one processor, storage, and a communication platform connected to a network for providing visual assistance to a user during a medical procedure involving a soft organ, the method comprising:
segmenting a soft organ and surrounding anatomical structures of the soft organ from image data obtained from a patient;
generating a three dimensional image of the soft organ and the surrounding anatomical structures of the soft organ based on the segmentation;
tracking location and orientation of a surgical instrument when the surgical instrument moves inside the patient's body during the medical procedure;
placing a corresponding virtual surgical instrument, based on the tracked location and orientation of the surgical instrument, in a 3D scene to reveal a relative spatial relationship of the surgical instrument with respect to the soft organ;
generating one or more images based on location and orientation of the corresponding virtual surgical instrument in the 3D scene, wherein the one or more images represent close-up views acquired from certain distance back from the tip of the virtual surgical instrument, and the distance is set based on an input from the user;
wherein at least one in-scene control is embedded in a border of at least one of the one or more images; and
simultaneously displaying the three dimensional image with the surgical instrument visualized therein in relation to the soft organ and the surrounding anatomical structures and the one or more images.

* * * * *